(12) United States Patent
Fox

(10) Patent No.: US 9,907,585 B2
(45) Date of Patent: Mar. 6, 2018

(54) BONE INTRAMEDULLARY FIXATION SCAFFOLD

(71) Applicant: William Casey Fox, Pipe Creek, TX (US)

(72) Inventor: William Casey Fox, Pipe Creek, TX (US)

(73) Assignee: William Casey Fox, Pipe Creek, TX (US)

( * ) Notice: Subject to any disclaimer, the term of this patent is extended or adjusted under 35 U.S.C. 154(b) by 0 days.

(21) Appl. No.: 15/040,789

(22) Filed: Feb. 10, 2016

(65) Prior Publication Data

US 2016/0317198 A1 Nov. 3, 2016

Related U.S. Application Data

(60) Provisional application No. 62/155,032, filed on Apr. 30, 2015.

(51) Int. Cl.
*A61B 17/72* (2006.01)

(52) U.S. Cl.
CPC ...... *A61B 17/7225* (2013.01); *A61B 17/7258* (2013.01); *A61B 17/7275* (2013.01); *A61B 17/7291* (2013.01)

(58) Field of Classification Search
CPC ............ A61B 17/7225; A61B 17/7233; A61B 17/725; A61B 17/863; A61B 17/869; A61B 17/8858; A61B 17/7275; A61B 17/7258; A61B 17/70; A61B 17/7097; A61B 17/1617; A61B 17/8811; A61B 17/7098;

(Continued)

(56) References Cited

U.S. PATENT DOCUMENTS 7,942,875 B2 *  5/2011  Nelson ............... A61B 17/7208
                                                            606/63
7,959,652 B2 *  6/2011  Zucherman ........ A61B 17/7065
                                                            606/249

(Continued)

*Primary Examiner* — Pedro Philogene
(74) *Attorney, Agent, or Firm* — Dickinson Wright PLLC; Ross Spencer Garsson

(57) ABSTRACT

A new shape changing bone implant and instrument for the fixation of structures to include bone tissue. This new implant stores elastic mechanical energy to exert force on fixated structures to enhance their security and in bone affect its healing response. This unique implant locks into bone and then simultaneously expands and shortens to lock into bone and then pull the bone segments together. This implant once placed changes shape in response to geometric changes in the implant's and bone's materials structure. The implant may be fabricated from any biocompatible material that acts elastically when deformed including but not limited to nitinol, stainless steel, titanium, and their alloys as well as polymers such as polyetheretherketone, silicone elastomer and polyethylene. The implant is advanced over prior devices due to its: (1) method of operation, (2) high strength, (3) method of insertion, (4) compressive force temperature independence, (5) energy storing implant retention and delivery system, (6) compatibility with reusable or single use product configuration, (7) ability to act as a scaffold to conduct healing bone through the implant, (8) efficient and cost effective manufacturing methods, and (9) reduction in the steps required to place the device.

20 Claims, 13 Drawing Sheets

(58) Field of Classification Search
CPC . A61B 17/742; A61B 17/844; A61B 17/8685;
A61B 17/866; A61B 17/864; A61B
2017/8655; A61B 17/00867; A61B
17/564
USPC .............................. 606/62–64, 75, 331, 300
See application file for complete search history.

(56) References Cited

U.S. PATENT DOCUMENTS

| | | |
|---|---|---|
| 8,394,097 B2 | 3/2013 | Peyrot et al. |
| 8,475,456 B2 | 7/2013 | Augoyard et al. |
| 8,556,949 B2 * | 10/2013 | Teisen .................... A61B 17/68 606/323 |
| 8,584,853 B2 | 11/2013 | Knight et al. |
| 8,834,483 B2 | 9/2014 | Cheney et al. |
| 9,101,349 B2 | 8/2015 | Knight et al. |
| 9,138,274 B1 * | 9/2015 | Biesinger ............. A61B 17/844 |
| 9,161,789 B2 | 10/2015 | Peyrot et al. |
| D745,163 S | 12/2015 | Cheney et al. |
| 9,204,932 B2 | 12/2015 | Knight et al. |
| 2002/0165544 A1 | 11/2002 | Perren et al. |
| 2004/0133204 A1 * | 7/2004 | Davies ............... A61B 17/7266 606/63 |
| 2009/0182336 A1 * | 7/2009 | Brenzel ............. A61B 17/7225 606/62 |
| 2015/0201979 A1 * | 7/2015 | Paul .................. A61B 17/7266 606/62 |

\* cited by examiner

BONE INTRAMEDULLARY FIXATION SCAFFOLD

CROSS-REFERENCE TO RELATED PATENT APPLICATION

This application claims priority to U.S. Patent Appl. Ser. No. 62/155,032, filed Apr. 30, 2015, entitled "Bone Intramedullary Fixation Scaffold," which is hereby incorporated herein by reference in its entirety for all purposes.

TECHNICAL FIELD

This application relates to implants used for fixation of bone of the musculoskeletal system and the methods for their use and more specifically to implants that reside within bone and that are caused to change shape through their metallurgic properties and their interaction with mechanical instruments to pull together and compress bone.

BACKGROUND

Bone screws and wires have been in clinical use for decades for bone fixation. These important bone fixation devices have evolved from rigid stainless steel or titanium wires and screws to shape changing nitinol implants that through their expansion are fixated in bone. These implants are commonly placed along the centerline of bone and thus reside within the bone's intra-medullary canal.

The early rigid bone fixation devices were commonly threaded or drilled into bone where the more modern devices are implanted in drilled holes and expand through mechanical means to lock into bone but none, other than the invention described herein, lock into bone and then shorten to pull together and compress the bony segments. Intramedullary bone fixation technology includes: (1) wires, (2) screws, (3) multi-component screws, (4) heat sensitive shape memory alloy implants cut from plates, and (5) polymer pins intended to degrade over time.

The implant embodiments of the present invention have advantages over the prior art because they store mechanical energy and impart that energy to bone through shape change and predictable bone-to-bone compression. The implant embodiments of the present invention pull together and compress bone to promote healing. The implant embodiments of the present invention are hollow, which allow bone to grow within the implants so as to further lock the implant into bone and conduct new bone through the implants' lumen to bridge bones intended to heal together.

Some prior art implants may change shape or be caused to change shape but do not lock into the separate bone segments and then act to pull together and compress bone.

Instruments, to place the implants into bone, complements the implants' method of action by holding the implants extended and at their minimum diameter, allowing the implants to be manipulated in bone, releasing the implants when fully inserted, and protecting the implants during handling and shipment.

As will be clear in the following detailed description of the prior art, the embodiments disclosed and taught in the present Application overcome the prior art deficiencies in ease of use, manufacturing, mode of operation, strength, cost and allows hospital procedures that limit disease transmission.

Expanding and Bone Locking Implants

The embodiments of the present invention overcome the deficiencies of other within bone fixation implants such as (1) requiring heating or cooling, (2) having a temperature dependent fixation force, (3) requiring ancillary equipment to manipulate the implant, (4) being implanted in the soft martensitic phase of nitinol, (5) requiring an expensive multiple step manufacturing process to set both the staple shape and transition temperatures, and (6) others that become more clear in the review of the embodiments of the present invention.

The embodiments of the present invention overcome the deficiencies of the prior elastic staples and intramedullary bone shape changing bone fixation devices such as (1) providing the surgeon limited time to place it in bone, (2) designs that cannot contract their length, (3) requiring expensive ancillary equipment to manipulate the implant, (4) cooling of the implant prior to opening for placement, (5) designs that can not simultaneously expand to lock into bone and contract to pull together and compress bone, and (6) others deficiencies that will become more clear in the review of the embodiments of the present invention.

Instrument and Implant Devices and Methods

The foregoing discussion illustrates the deficiencies of the prior art and the lack of a simple shape changing bone fixation implant, instrument for its implantation and method of use consistent with the demands of surgery. Product packaging may be in reusable hospital sterilization tray and a manufactured sterile kit containing the implant and instruments required for surgery. In the discussion of the embodiments of the subject invention its benefits will be realized as a simple, reliable, low cost solution to present an elastic energy storing shape changing staple to bone and releasing the staple so that it can pull together and compress bone even in the presence of gaps that can form during bone healing.

SUMMARY OF THE INVENTION

The embodiments of the subject invention describe an improved within bone fixation implant that stores recoverable mechanical energy in its structure and changes shape to pull together and compress the bone fixation interface. Any biocompatible that has structural properties and behaves elastically when deformed such as but not limited to nitinol, titanium, and stainless steel, as well as a number of polymers polyetheretherketone, silicone elastomers and polyethylene. This implant, instrument, and method have multiple advantages over prior implants: (1) shape change and compression forces are temperature independent, (2) the implant does not require heat or cooling to activate it, (3) the implant does not need to be stretched or mechanically manipulated by the surgeon to facilitate implantation, (4) the surgeon's sole required effort, pushing the implant into bone and releasing it while the implant automatically controls the implant mechanism of shape change and compression, (5) the implant load transfer to bone can be controlled by the surgeon with its instrument to minimize the chance of implant induced fracture and (6) the implant's bone fixation load is at a maximum and constant during the operative procedure.

In certain embodiments, this implant-containing instrument is combined with a reusable or disposable extrusion instrument for pushing the implant through the instrument and into bone. This allows the use of shape changing implants in reusable and disposable instruments which are pre-sterilized in procedures and under conditions in which the prior art staples cannot be used.

In general, in one aspect, the invention features a fixation device that includes a body that is operable to change shape to expand and shorten the body. The body includes an elastic material. The body has a plurality of prongs on each of a first end and a second end. The body has a shortening section between the prongs on the first end and the second end. The shortening section is operable to shorten the body by moving from an elongated position to a shortened position.

Implementations of the invention can include one or more of the following features:

The body can be a tubular shape.

The shortening section can form an expanded bulge when operated to shorten the body.

The expanded bulge can be oriented with the long axis of the body.

The fixation device can further include an internal mandrel. The shortening section can be held in the elongated position with the internal mandrel.

The internal mandrel can include grooves to receive a locking plate.

The internal mandrel can include a cross sectional shape in a first section of the internal mandrel. The first cross sectional shape can be different in shape than other sections of the internal mandrel.

The cross sectional shape can be a square shape, a rectangular shape, a hexagonal shape, a triangular shape, or a non-round shape.

The fixation device can further include a lock plate and a lumen. The lock plate can be integral to the lumen.

The lock plate can be operable to interact with the internal mandrel so that the lock plate is operable to rotate between a locked position and an unlocked position.

The fixation device can further include an external sleeve. The shortening section can be held in the elongated position with an external sleeve.

The fixation device can further include a plurality of fenestrations and a lumen. The fenestrations can provide openings into the lumen.

The fenestrations and lumen can be positioned to allow bone ingrowth into the body.

The first end can be slotted and the second end can be slotted so that each of the first end and the second end is capable of bending to conform to the internal anatomy of bone.

The prongs in the plurality of prongs can extend outward from the body.

The prongs can be twisted in a twist direction.

The twist direction of the prongs can be positioned so that when the body is turned in a first direction the prongs deflect inward.

The twist direction of the prongs can be positioned so that when the body is turned in a second direction the prongs deflect outward.

The fixation device can be operable for use in a medical procedure.

The elastic material can include an elastic metal that is nitinol, stainless steel, titanium, or an alloy thereof.

The elastic material can include an elastic polymer that is polyetheretherketone, silicone elastomer, polyethylene, or a combination thereof.

In general, in another aspect, the invention features a method of fixating a first bone and a second bone. The method includes the step of selecting an implant having a first bone locking feature at a first end and a second bone locking feature at a second end. The method further includes the step of locking the first bone locking feature to the first bone. The method further includes the step of locking the second bone locking feature to the second bone. The method further includes the step of shortening the implant between the first bone locking feature and the second bone locking feature.

Implementations of the invention can include one or more of the following features:

The implant can allow bone ingrowth.

The implant can have an expandable surface. The method can further include expanding the expandable surface to lock into the first bone or the second bone.

The step of shortening the implant can include expanding a surface of the implant to shorten length of the implant.

The step of shortening the implant can include contacting an outer surface of the implant to shorten its length.

The shortening of the implant can impart mechanical energy to provide interfacial pressure between the first bone and the second bone.

The step of providing interfacial pressure can stimulate healing of the first bone and the second bone.

In general, in another aspect, the invention features a method of fixating a first bone and a second bone. The method includes the step of making holes in the first bone and the second bone to receive an implant. The method further includes the step of inserting a first end of the implant into the first bone. The method further includes the step of releasing the implant to change shape of the implant within the first bone. The method further includes the step of placing the second bone over a second end of the implant. The method further includes the step of pushing the first bone and the second bone together until the first bone contacts the second bone.

In general, in another aspect, the invention features a fixation device that includes a body that is operable to change shape from a first shape to a second shape. The first shape has a different length than the second shape. The body includes an elastic material. The body has a plurality of prongs on each of a first end and a second end. The body has a length changing section between the prongs on the first end and the second end. The length changing section is operable to change the length of the body by moving from a first length position to a second length position in which the first length position and the second length position are positions having different lengths.

Figure 1A:
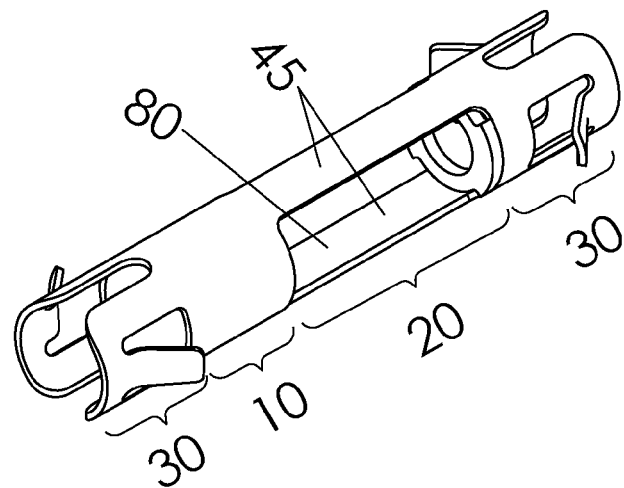
FIG. 1a depicts an embodiment of the present invention of an implant of in its constrained configuration.

REFERENCE NUMERALS 10. tubular section
20. shape changing section
30. fixation section
40. bulge expanded
45. bulge contracted
50. prongs
60. push plate
70. conformation slots
80. lumen
90. lock plate
95. lock plate mandrel release opening
100. sleeve
110. handle
120. knob
130. knob unlock direction of movement
140. knob advancement direction of movement
150. knob implant release direction of movement
160. implant removal direction of movement for prong disengagement
170. prong twist angle
180. mandrel
190. mandrel head
200. proximal bone
210. distal bone
220. distal bone hole
230. proximal bone hole
300. internal locking prongs
310. internal prong locking tabs
320. external locking prongs
330. external prong locking tabs
340. mandrel for internal locking prongs
350. mandrel for external locking prongs
360. K-wire for alignment, creation of a pilot hole and fixating adjacent joints.
370. Drill bit
380. Drill stop
390. Drill bit handle
400. Direction of drill rotation
410. Removable lock pin and ring
420. Direction of knob rotation to release mandrel
430 Direction of advance of K-wire to treat adjacent joints
440 Lock plate integral to the IFS

DETAILED DESCRIPTION

The embodiments of the subject invention includes a tubular implant with a plurality of locking prongs 50, expanding and implant shortening bone locking bulges 40, fenestrations in its body, and a lumen 80 for bone ingrowth and instrument 110 operation.

The implant can be fabricated of any cross section not limited to round, square, hexagonal or triangular that can be formed with a lumen 80. The lumen 80 forms a hollow core to allow bone to form through the implant and bridge the bone segments it fixates.

Figure 6A:
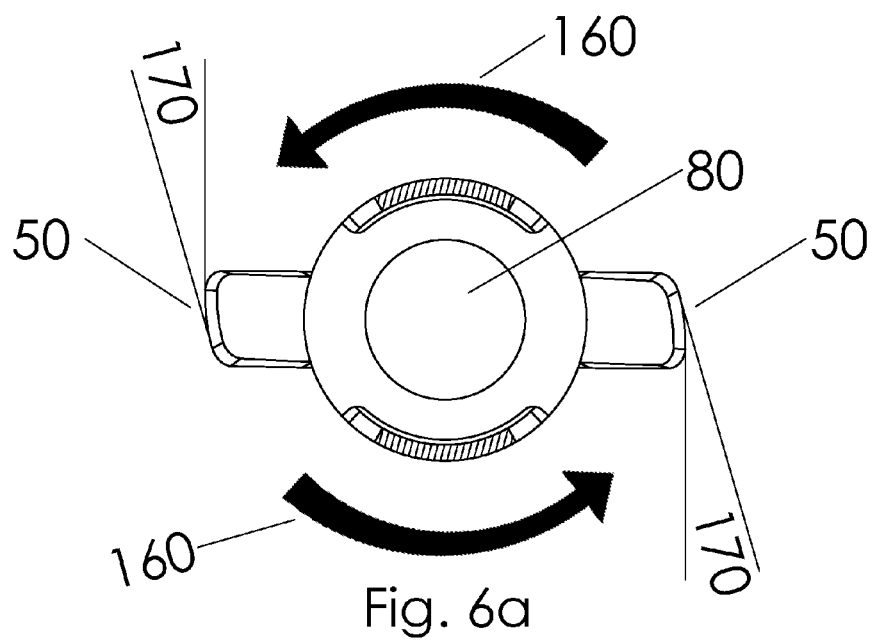
FIG. 6a depicts an end view of an implant of an embodiment of the present invention showing direction of rotation to cause disengagement of the prongs from bone.
Figures 6B, 6C:
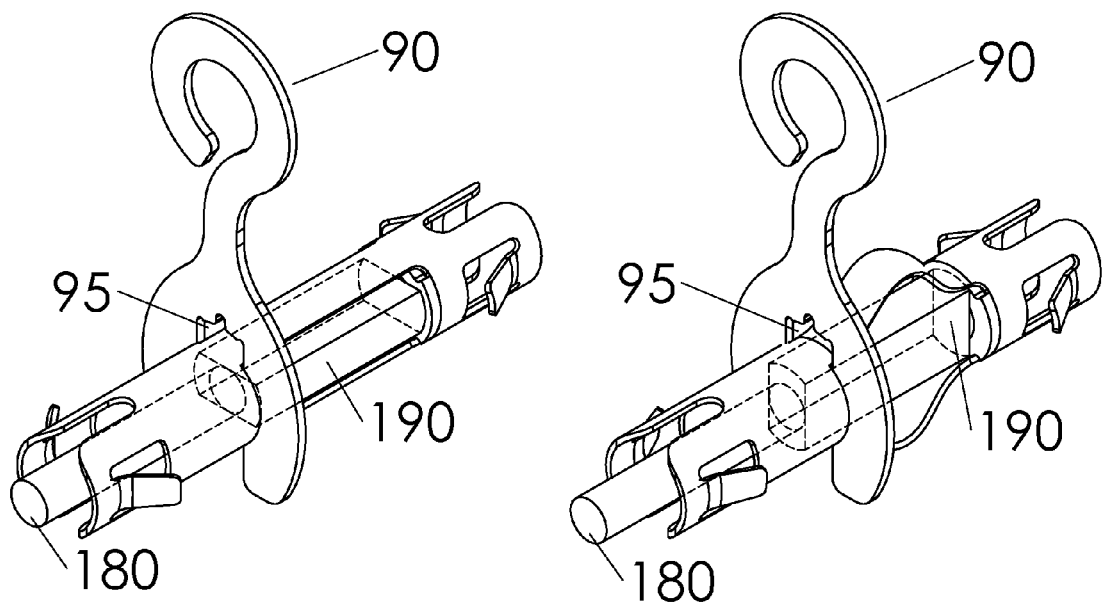
FIG. 6b depicts the implant of FIG. 6a with a mandrel and a lock plate in its constrained configuration.
FIG. 6c depicts the implant of FIG. 6a with the mandrel and the lock plate in its released configuration.

This lumen 80 further receives the instrument mandrel 180 to extend the implant's length and constrain the implant at its greatest length and minimum bulge 45 diameter. The mandrel has at least one section that is square, rectangular, hexagonal, triangular or other shape other than round. The mandrel 180, lock plate 90 and implant push plate 60 interlock to hold the implant extended, as illustrated in FIG. 6b. When the mandrel 180 is turned, it aligns with the lock plate slot 95 removing the implant's constraint and allowing the implant to shorten and the bulges 40 to be in their extended state. The lock plate (440) can be integral to the body and contained within the lumen (80) in an alternate embodiment where the lock plate is not removable.

The prongs 50 and bulge 40 lock into bone to resist implant rotation and pull out and pull the bones together to create compression. If implant loosening occurs the bulges 40 will continue to expand further shortening the implant and causing it to keep pulling the bones together.

Figure 1B:
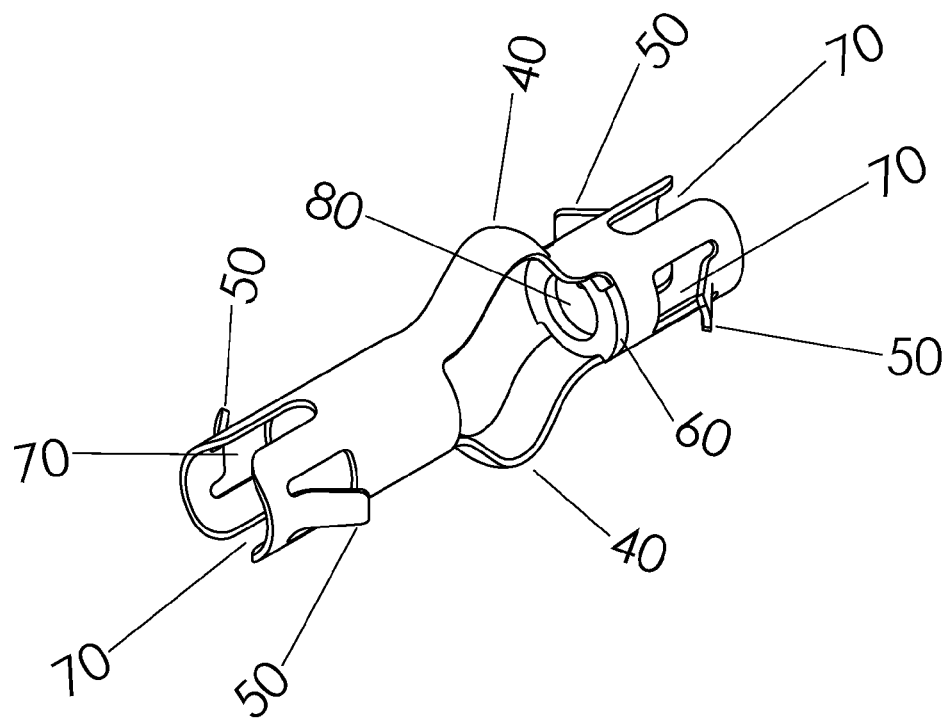
FIG. 1b depicts the implant of FIG. 1a in its released configuration.
Figure 2A:
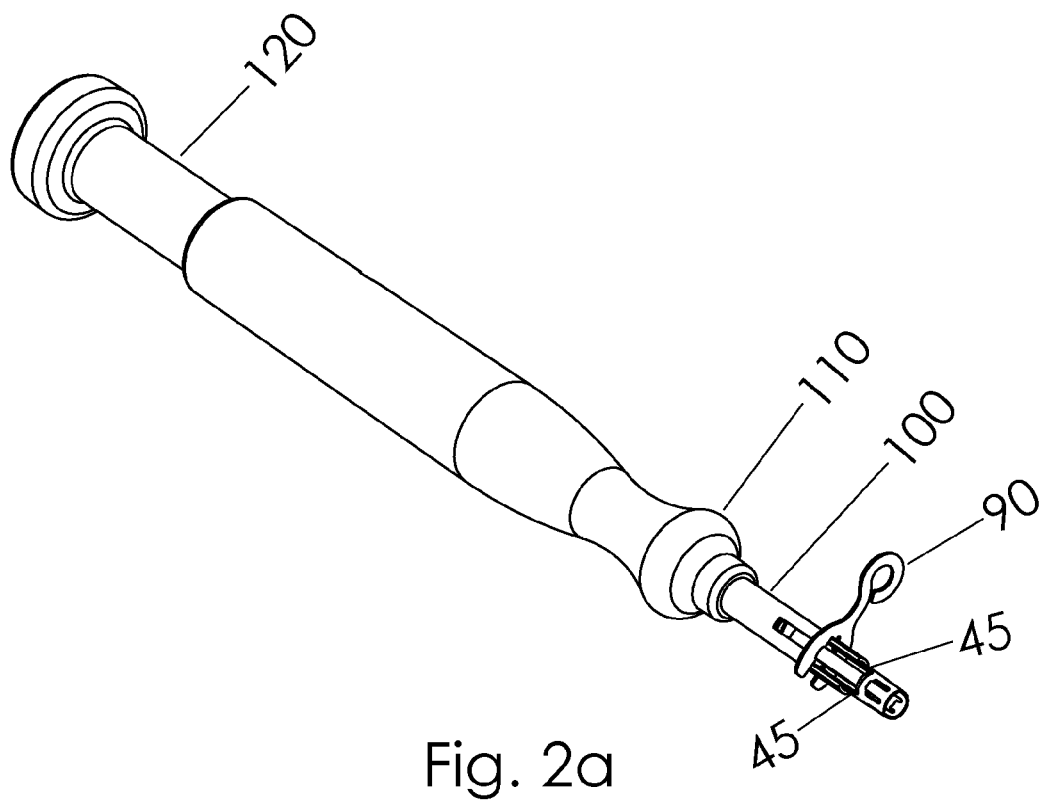
FIG. 2a depicts an embodiment of the present invention of an implant constrained with in its instrument.
Figure 2B:
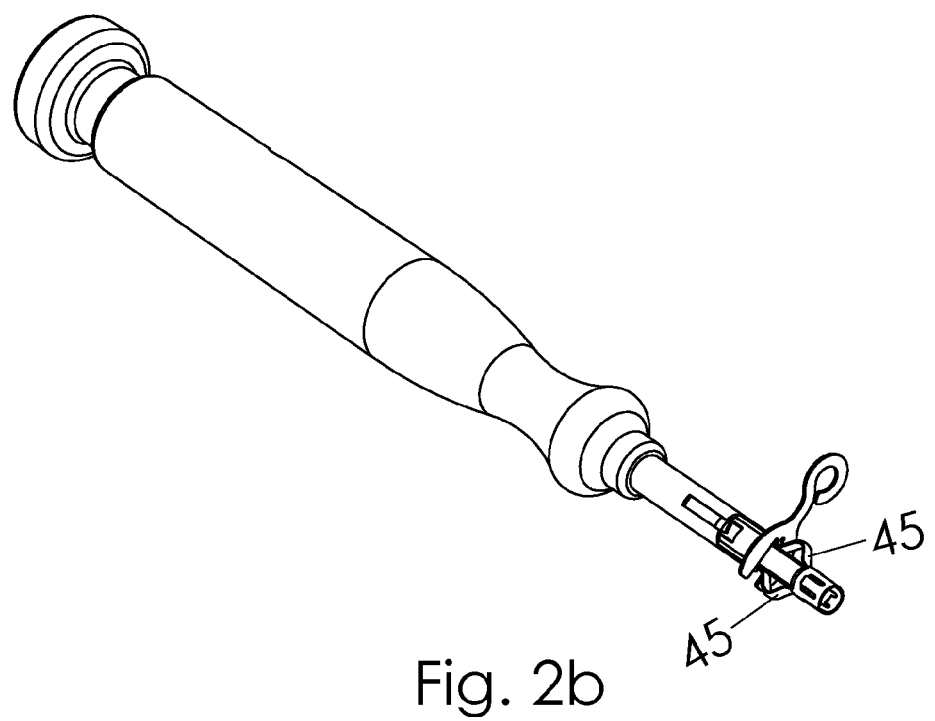
FIG. 2b depicts the implant and instrument of FIG. 2a with the implant released within its instrument.

The constrained implant state of FIG. 1a and the unconstrained state of FIG. 1b illustrate the shape change that occurs to the implant when release with the instrument. In use, the implant is held within an instrument 110 with an advance and release knob 120 as shown in FIG. 2a. The instrument has a sleeve 100 that constrains the implant and protects it from inadvertent release and resist rotation of the implant through interlocking features with the prongs 50 and lock plate 90. Alternatively, sleeve 100 can be omitted and a separate component protective end cap can be placed over the implant and instrument to constrain and protect the implant. When the lock knob 120 is advanced and turned within the instrument 110, the implant is released and the bulges 40 extend as shown in FIG. 2b.

Figure 3A:
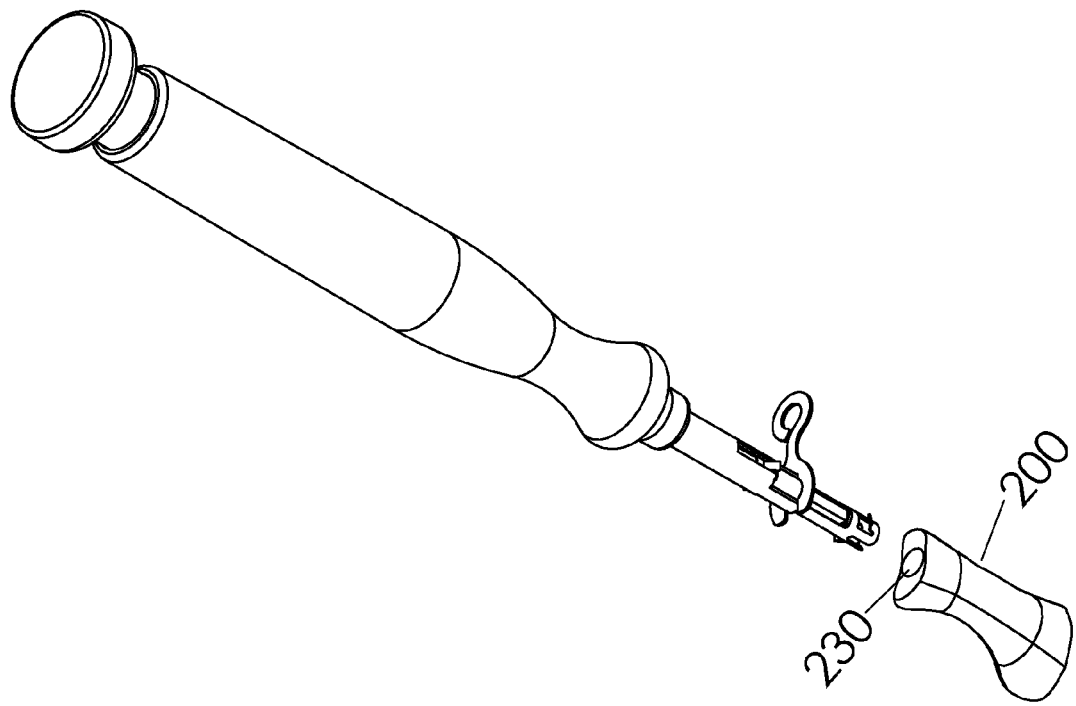
FIG. 3a depicts the implant and instrument of FIG. 2a with the implant advanced and constrained within its instrument in preparation for implantation into bone.
Figure 3B:
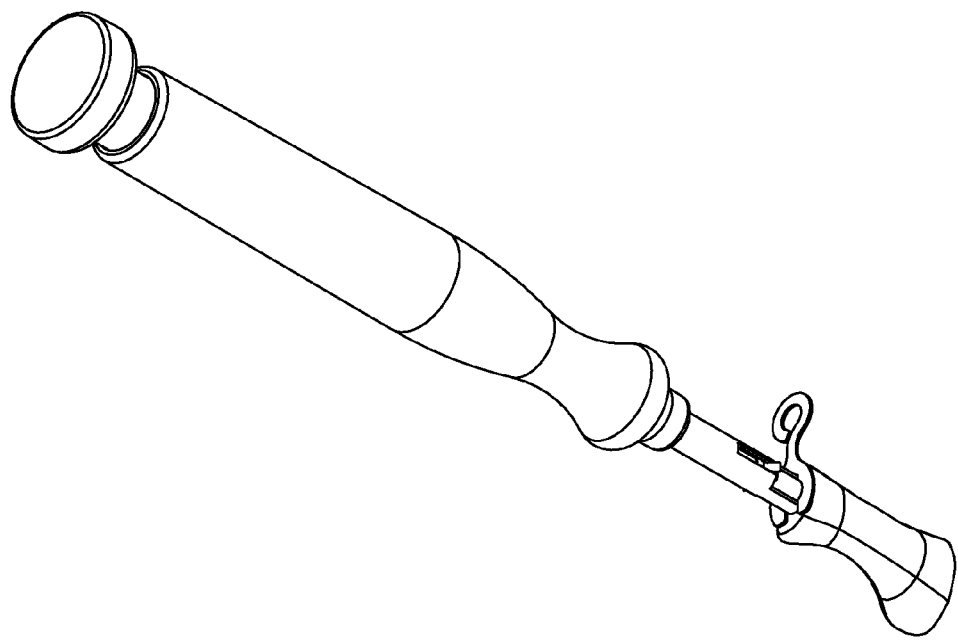
FIG. 3b depicts the implant and instrument of FIG. 2a with the implant within bone prior to implant release.
Figure 4A:
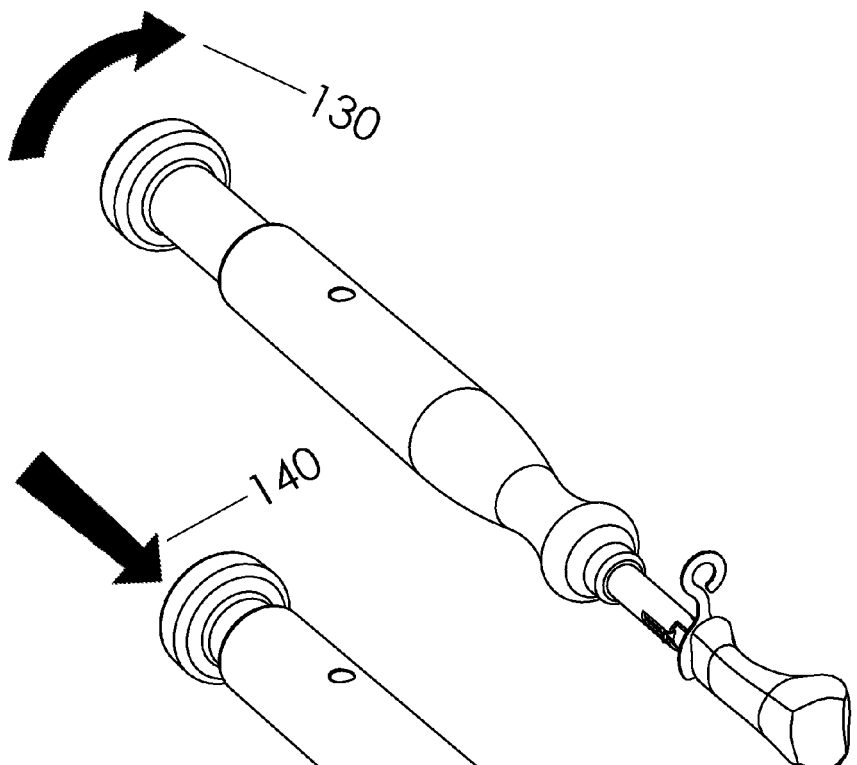
FIG. 4a depicts the implant and instrument of FIG. 2a with the implant constrained within instrument showing instrument unlocking.
Figure 4B:
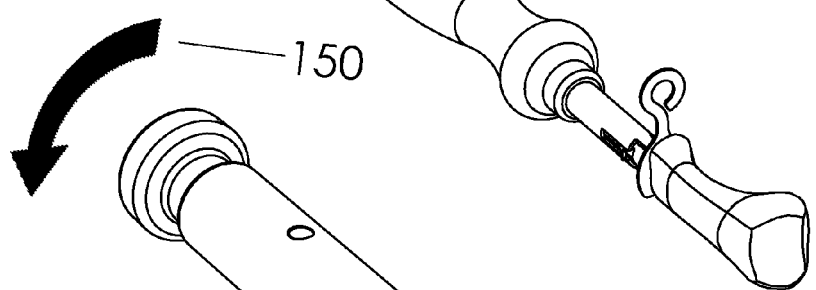
FIG. 4b depicts the implant and instrument of FIG. 2a with the implant being advanced through the instrument into bone.
Figure 4C:
FIG. 4c depicts the implant and instrument of FIG. 2a with the implant showing instrument release.

Implantation into a drill hole 230 in bone 200 is illustrated in FIG. 3a, where the implant is positioned for placement, and in FIG. 3b, where the implant is advanced until it is fully within bone and the lock plate 90 is in contact with the end face of the bone. Once the implant is in position, the lock knob 120 is turned in direction 130 to release the lock knob 120 so that it can be advanced in direction 140 with the implant as shown in FIG. 4a and FIG. 4b. Once advanced the lock knob 120 is turned in direction 150, and the implant is released as shown in FIG. 4c. An alternate embodiment exist that does not require the implant to be advanced out of the instrument 110 and only requires the lock knob 120 to be turned to release the implant. This embodiment uses the protective end cap.

Figure 5A:
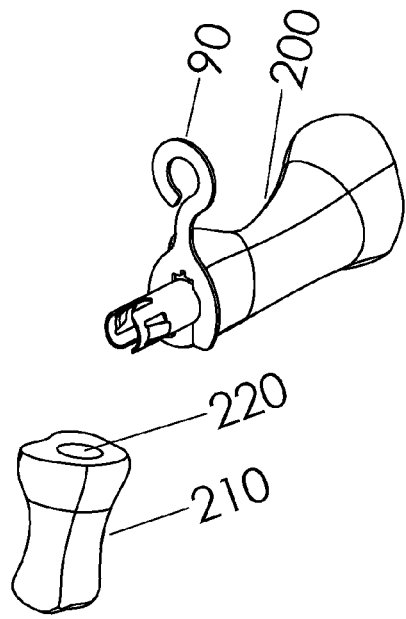
FIG. 5a depicts an implant of an embodiment of the present invention in a first bone.
Figure 5B:
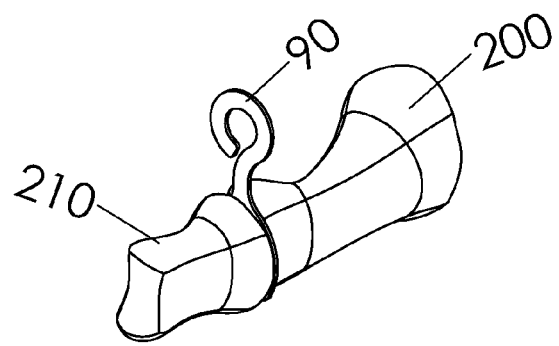
FIG. 5b depicts the implant of FIG. 5a with the implant in the first bone and a second bone with a lock plate.
Figure 5C:
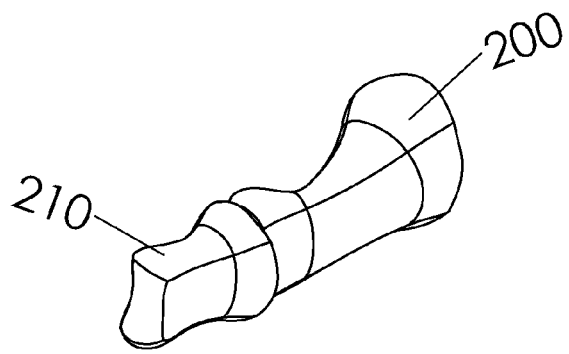
FIG. 5c depicts the implant of FIG. 5a with the implant in the first and second bone.

The instrument is then withdrawn from the implant so that a first end of the implant is within bone 200 and the second end extends beyond bone as shown in FIG. 5a. The second bone 210 is then placed so that its drill hole 220 covers the second end of the implant as shown in FIG. 5b. Once the bones are approximated, the lock plate 90 is pulled from the implant at the bone interface allowing bone to bone contact to occur as shown in FIG. 5c.

The implant prongs 50 have a twist along their central axis so that they are at an angle 170 with the body of the implant. This twist allows the implant to be rotated and pulled from bone as shown in FIG. 6a, if removal is required. When rotated counter clockwise (direction 160), the prongs 50 deflect towards the implant centerline and disengage bone allowing a twisting and pulling motion to remove the implant.

Figure 7A:
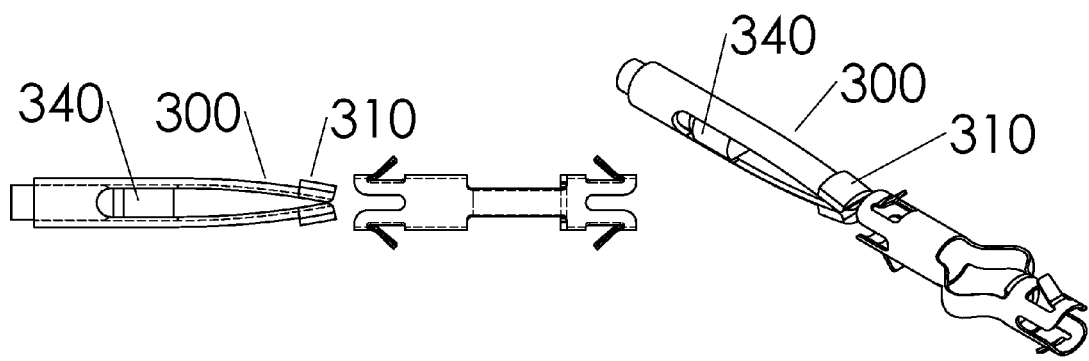
FIG. 7a depicts an embodiment of an alternate implant holding mechanism with prongs and mandrel.
Figure 7B:
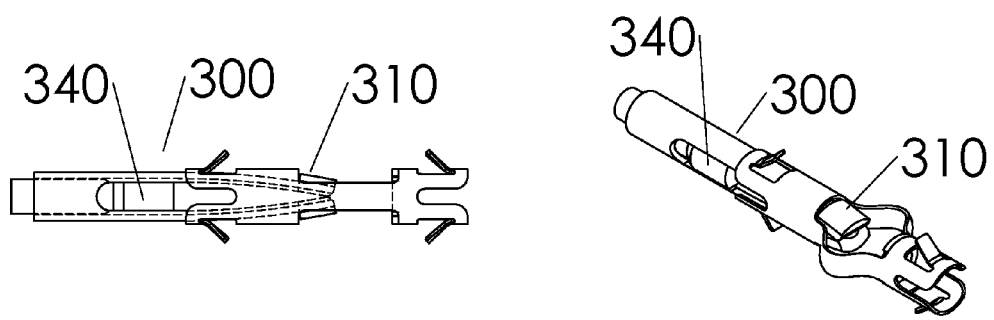
FIG. 7b depicts the implant holding mechanism of FIG. 7a with the alternate implant holding mechanism within an unconstrained implant lumen.
Figure 7C:
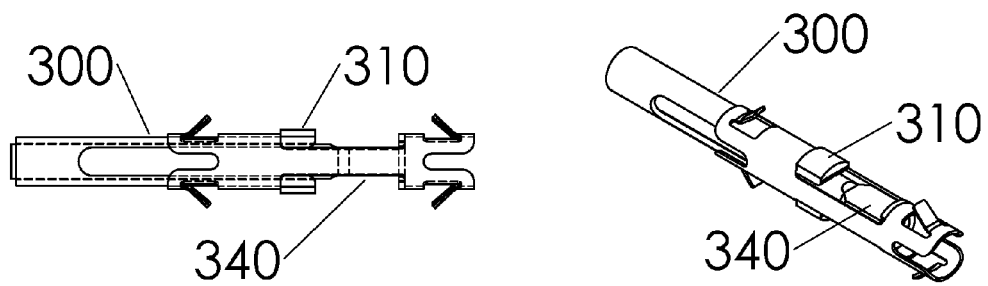
FIG. 7c depicts the implant holding mechanism of FIG. 7a with the alternate implant holding mechanism locked into constrained implant.
Figure 8A:
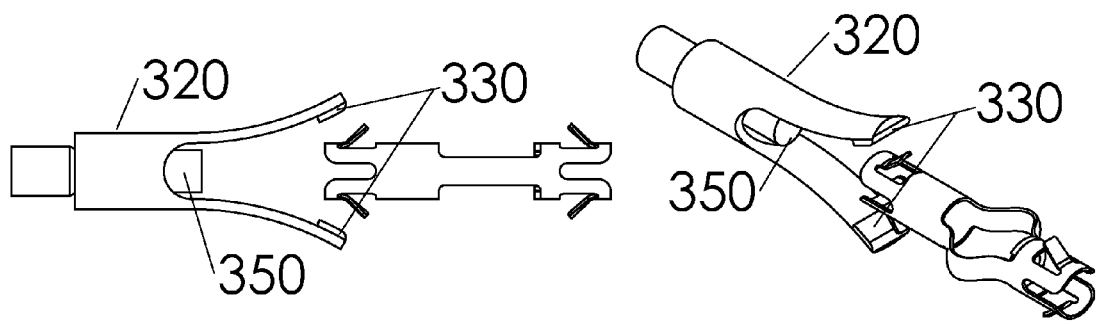
FIG. 8a depicts an embodiment of an alternate external implant holding mechanism and mandrel adjacent to unconstrained implant.
Figure 8B:
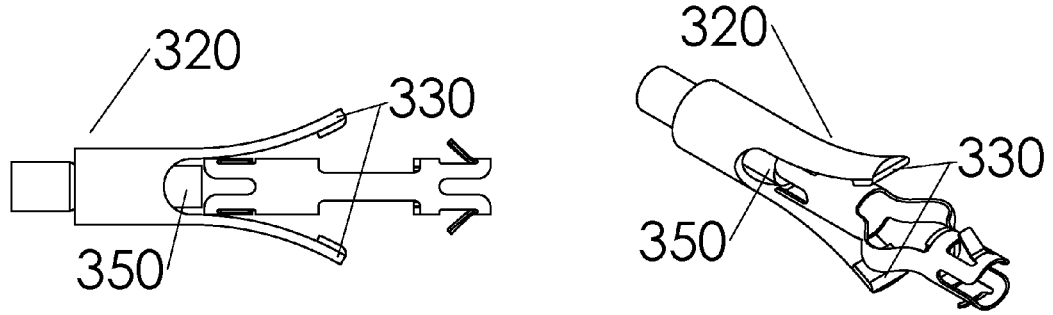
FIG. 8b depicts the implant holding mechanism of FIG. 8a with the alternate external implant holding mechanism and mandrel within and overlapping unconstrained implant.
Figure 8C:
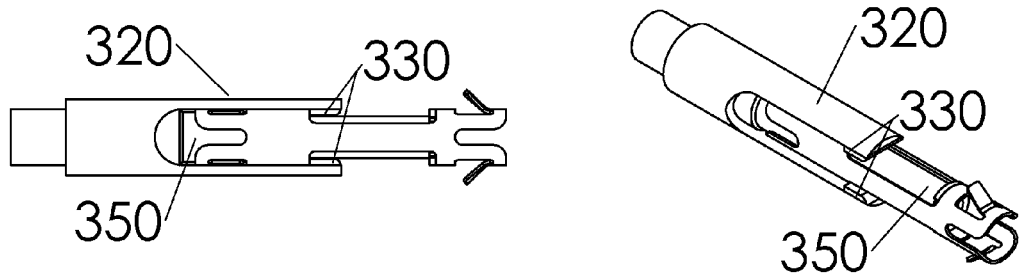
FIG. 8c depicts the implant holding mechanism of FIG. 8a with the alternate external implant holding mechanism and mandrel locked into constrained implant.

Alternate embodiments of the mandrel 340 can be used with an internal locking prongs 300 with tabs 310 to hold the implant and extend its length as shown in FIGS. 7a-7c. A second alternate embodiment of the mandrel 350 and external locking prongs 320 with tabs 330 can be used as shown in FIGS. 8a-8c.

The invention and its various embodiments are unique in that the implant first locks into a first bone and a second bone and then, when the mandrel 190 releases through the lock plate 90, the bulge 40 expands and shortens the implant. With both ends locked into bone, the expansion of the bulge 40 pulls together and compresses the bone at the healing interface. The implant is self-adjusting in that, if it loosens, the bulge 40 further expands, the implant shortens, and the bone is again pulled together and held in contact.

The action of the implant minimizes or eliminates any distance bone must grow to fuse the two bone segments. This lack of a gap between the bones further minimizes the possibility of soft tissue migrating between the bone segments and delaying healing. It is further believed that the interfacial pressure created may stimulate bone healing.

In other embodiments of the present invention, the implant can be designed to differently change in length, such as to extend to distract two bones. For instance, embodiments of the subject invention includes a tubular implant with a plurality of locking prongs, implant lengthening bone locking extenders, fenestrations in its body, and a lumen for bone ingrowth and instrument operation. Such implants can be utilized in applications in which the two bones are held and maintained in distraction.

This pre-sterilized combination instruments and implant can be packaged with a drill bit and wires so that the medical procedure kit fully supports the surgical technique. Hospital costs savings are achieved because there is no hospital cleaning or sterilization required and the patients and hospital benefit from fewer infections and patient complications.

OPERATION OF THE INVENTION

The implant embodiments are uniquely suited for fixation of materials that have a tendency to benefit from compression or shrink and withdraw so that the fixated structures lose contact. Without limiting the scope of the invention the illustrated embodiments are used for bone fixation. In bone surgery fragments, separated segments and segments requiring fixation are pulled together by the implant because it is inserted so that one end is in a first bone segment and the other end is in the second bone segment. This method of surgical use is common to bone fixation devices.

The shape changing implant, of the embodiments of the subject invention, exert bone compression force that is not temperature dependent. This provides tremendous advantage for the surgeon and patient over prior art nitinol shape changing implants.

Temperature independence solves problems with the prior art nitinol staples because the embodiments of the subject invention apply consistent force prior, during and following implantation. Body temperature implants' force changes as the operative wound warms from near room temperature to body temperature. This force increase occurs after the wound is closed and without the knowledge of the surgeon can create fracture or deformity.

During surgical use the surgeon inserts one end of the implant into a first bone so that the end, prongs and bulge are fully contained within the first bone. The instrument holding the implant elongated is operated to release the implant. When released the bulge expands pulling the implant deeper into bone until the implant lock plate resist the pulling forces of the implant. The second implant end is then positioned in a second bone and this bone is pushed so that the implant is fully contained within the two bones. Once the bones are in apposition the lock plate is pulled and the two bones are held in contact and under compression by the shape changing elements of the implant. Often treatment of the joints adjacent to where the implant is placed require temporary fixation. Surgeons commonly use a sharp tipped stiff wire. The implant uniquely allows a surgeon to advance a wire through the lumen of the implant into an adjacent joint.

The operation of embodiments can occur with or without the addition of heat. The preferred embodiment requires no heat other than that of the environment, room temperature. Alternate embodiments can be fabricated so that they change shape at body temperature or with higher temperatures caused by heating strategies such as conduction, induction or resistive heating.

First, the operation of the preferred embodiment is independent of temperature in the range of temperatures expected in clinical use and the use of nitinol. Thus tight control of the material's crystalline structure transition temperature is not required. Furthermore, the temperatures are set so that the material is always in its strong and high temperature austenitic form. Thus as long as the austenitic finish temperature is above 20° C. then it will be stable in the operating theater and patient's body. So fine chemistry control and post heat treatment to shift transition temperature is not required.

A surgical method for using the implant is illustrated in FIGS. 9-16. In the illustrated procedures, the implant within its instrument, the bone cutting instrument, and the wire have been removed from the sterile package. FIGS. 9-16 illustrate steps in the procedure.

Figure 9:
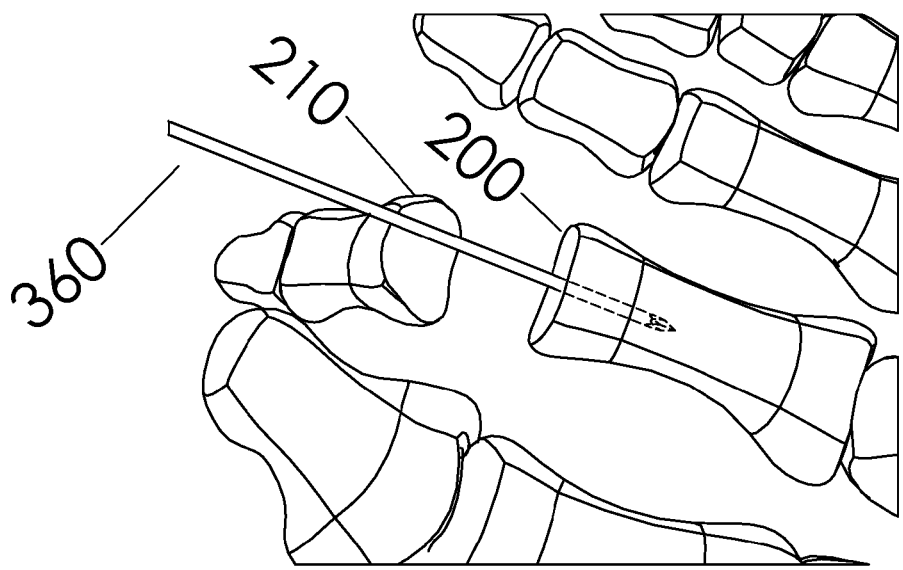
FIG. 9 depicts use of a K-wire (360) to create a pilot hole in the proximal bone (200).

As shown in FIG. 9, an alignment K-wire is used to create a pilot hole along the centerline of the bone.

Figure 10:
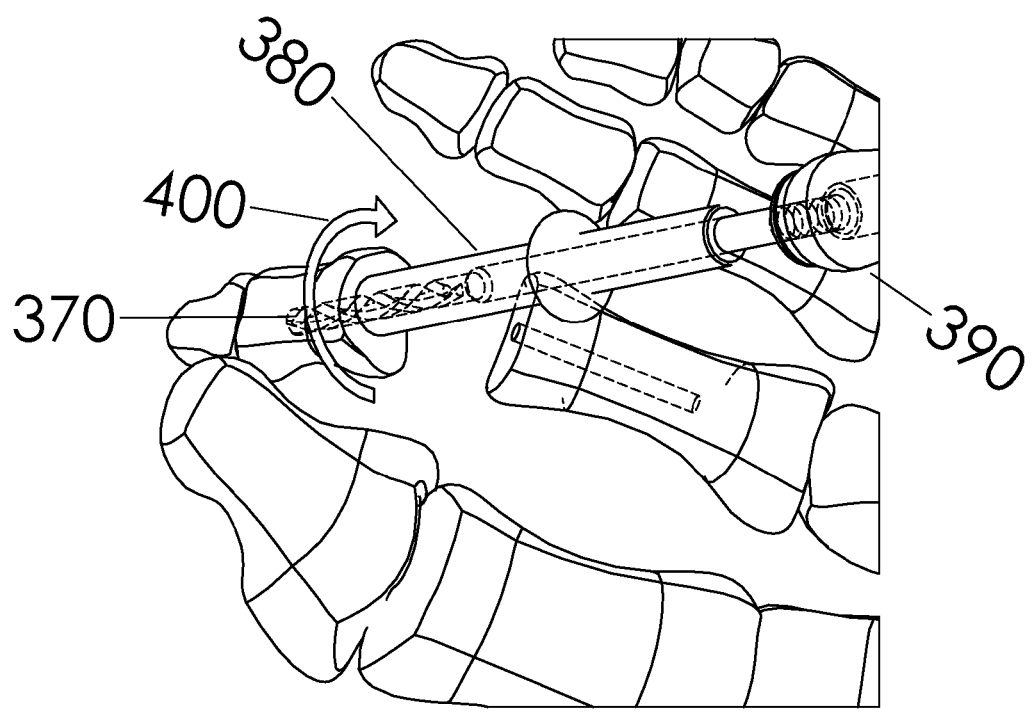
FIG. 10 depicts use of a drill (370) and drill stop (380) to drill a hole in the distal bone (210).

As shown in FIG. 10, a cutting instrument with depth stop is used to create a drill hole along the bone centerline of the distal bone.

Figure 11:
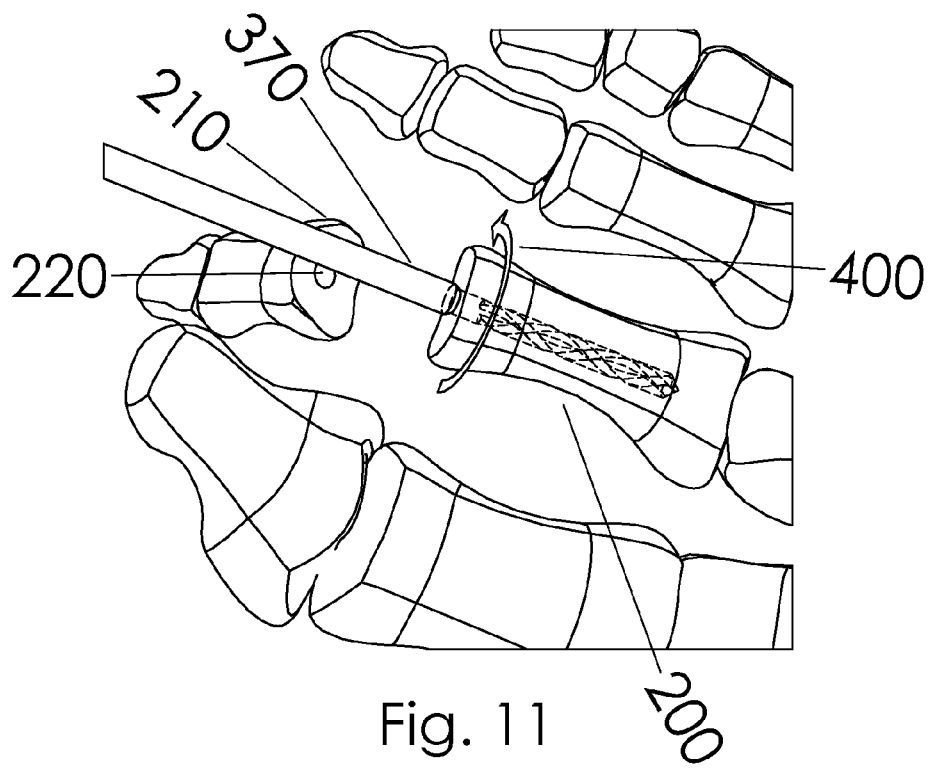
FIG. 11 depicts use of a drill (370) to drill a hole in the proximal bone (200).

As shown in FIG. 11, a cutting instrument with depth stop is used to create a drill hole along the bone centerline of the proximal bone.

Figure 12:
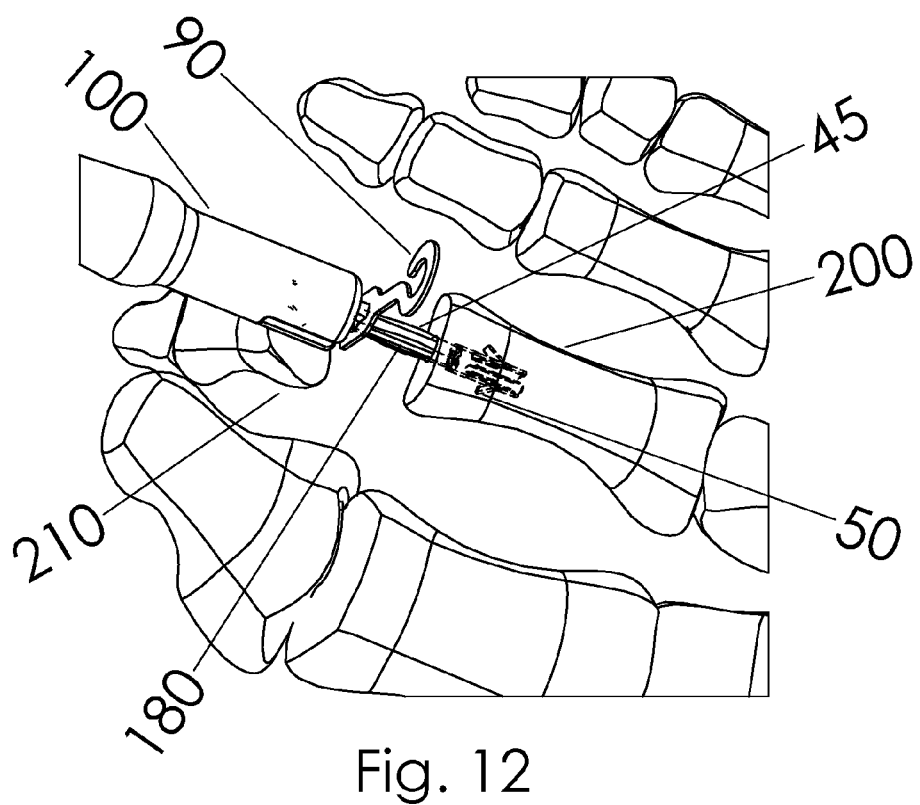
FIG. 12 depicts implantation of the intramedullary fixation scaffold in the proximal bone (200).

As shown in FIG. 12, the intermedullary fixation scaffold is inserted in the proximal bone drill hole.

Figure 13:
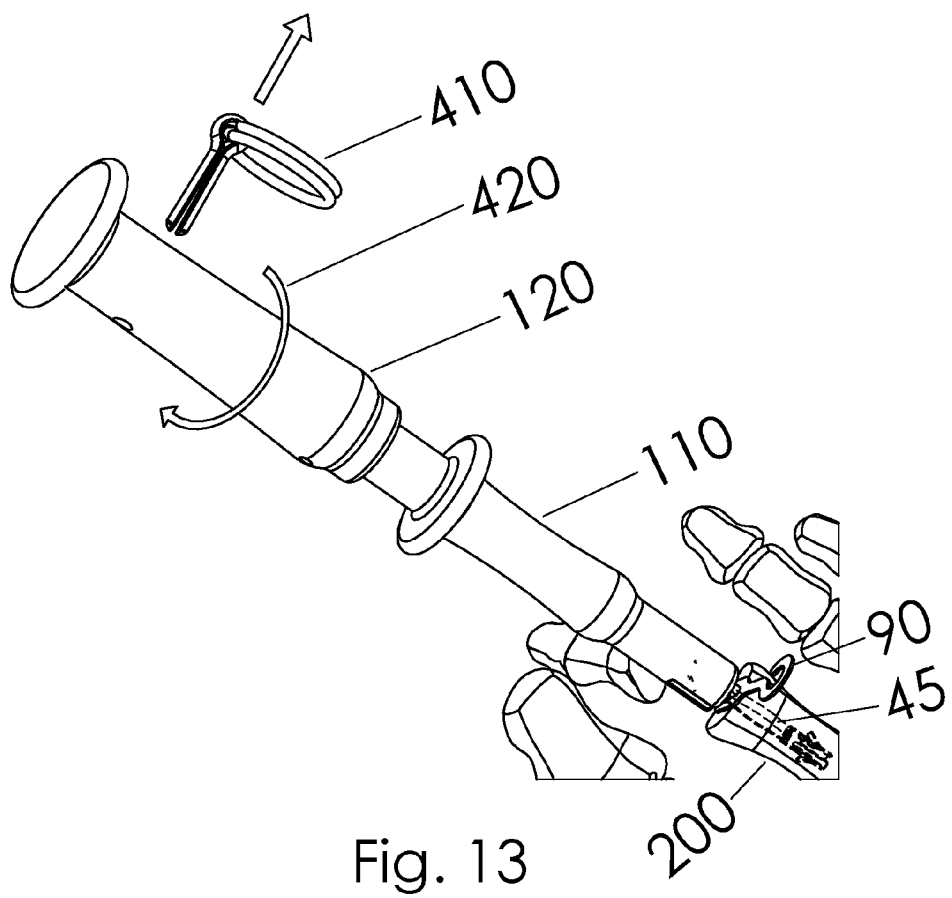
FIG. 13 depicts removal of a locking pin and ring (410) and rotation of the instrument knob (120) to release the intramedullary fixation scaffold in the proximal bone (200).

As shown in FIG. 13, the intermedullary fixation scaffold is unlocked and knob rotated to release the intermedullary fixation scaffold.

Figure 14:
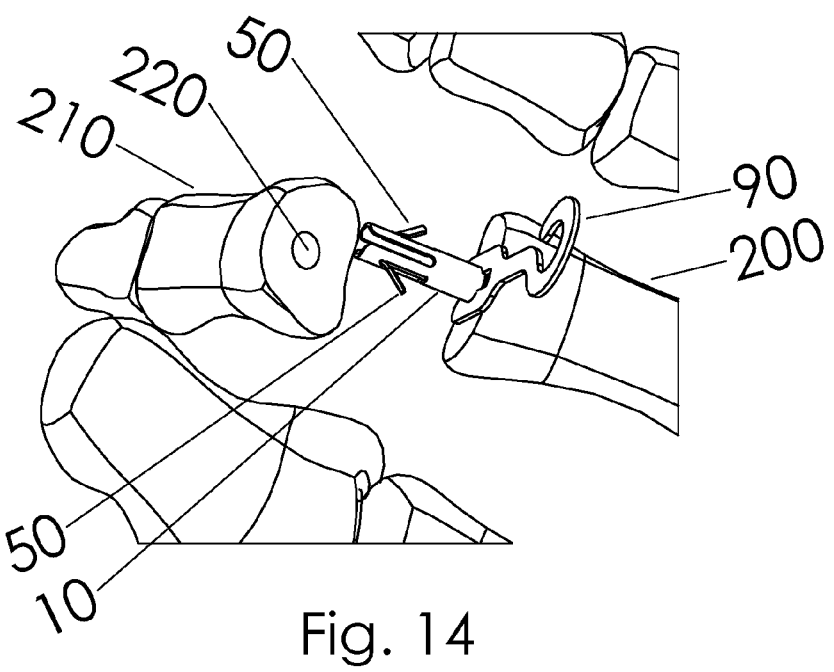
FIG. 14 depicts insertion of the intramedullary fixation scaffold in the distal bone drill hole (220).

As shown in FIG. 14, the distal end of the intermedullary fixation scaffold is positioned for insertion into the distal bone drill hole.

Figure 15:
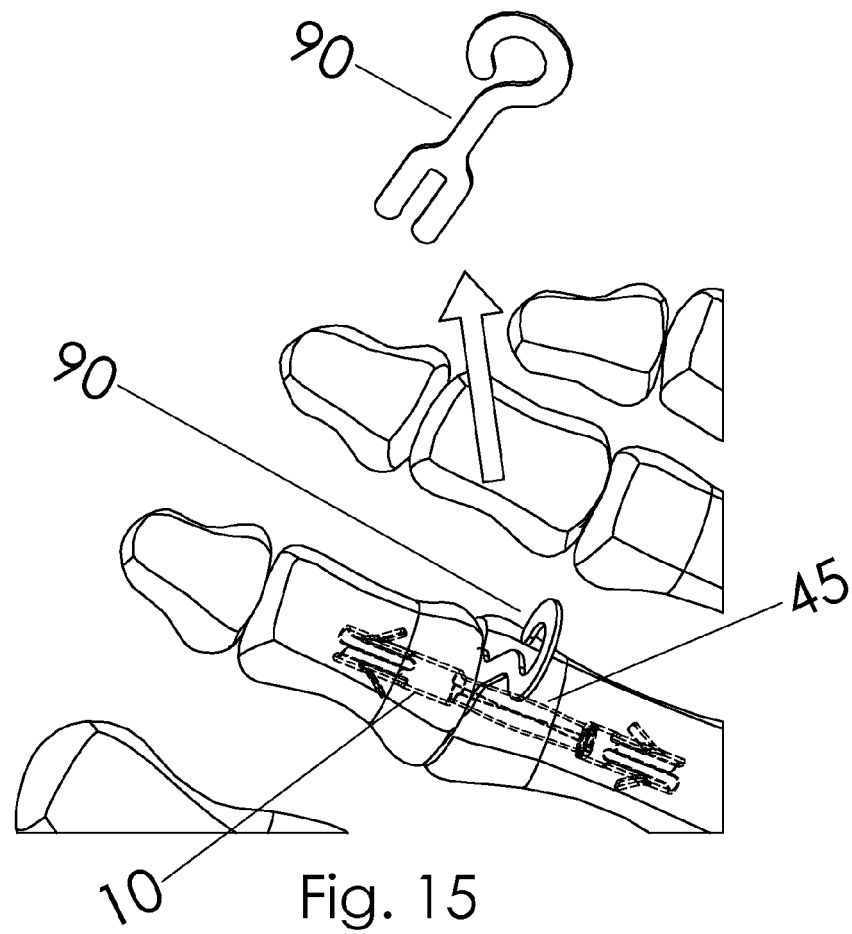
FIG. 15 depicts reduction of the distal bone on the proximal bone and removal of the lock plate (90).

As shown in FIG. 15, the distal and proximal bones are pushed together so that both bones contact the lock plate proceeding the lock plate removal.

Figure 16:
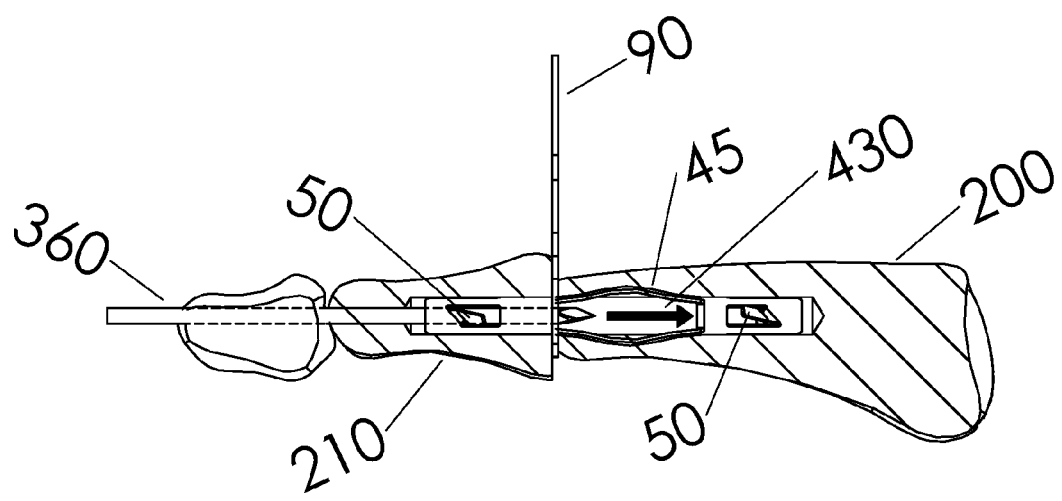
FIG. 16 depicts insertion of a k-wire (360) through an adjacent joint and through the intramedullary fixation scaffold.
Figure 17A:
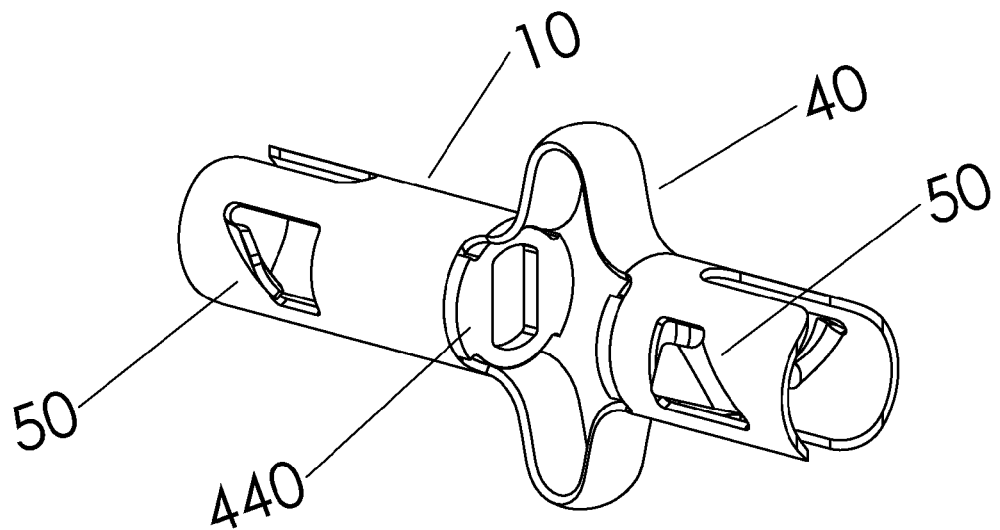
FIG. 17a depicts a lock plate (440) integral to the intramedullary fixation scaffold with the intramedullary fixation scaffold contracted in its length.
Figure 17B:
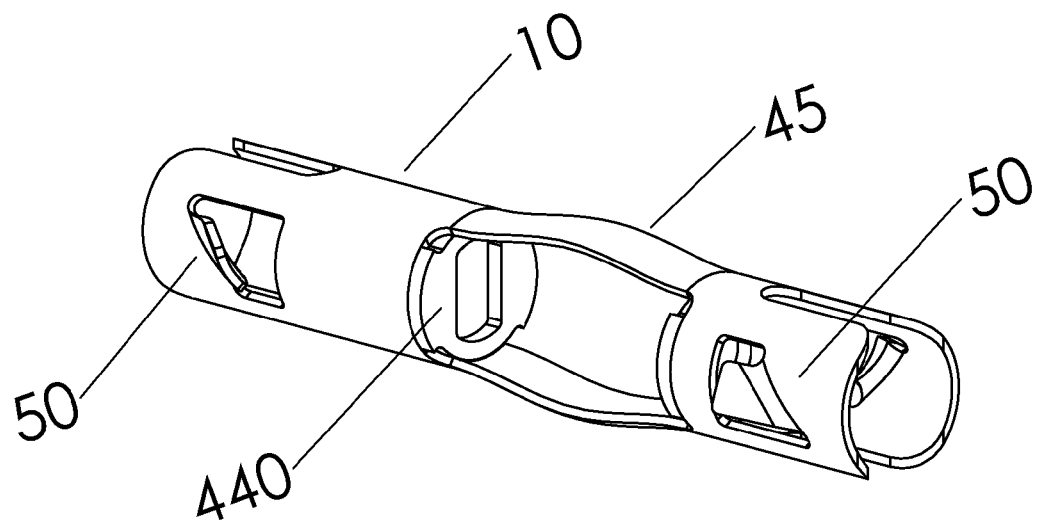
FIG. 17b depicts a lock plate (440) integral to the intramedullary fixation scaffold with the intramedullary fixation scaffold extended in its length.

As shown in FIG. 16, k-wire is inserted through an adjacent joint for its treatment, through the intermedullary fixation scaffold and if further advanced through a second adjacent joint.

CONCLUSIONS AND SCOPE

The embodiments illustrated in this application are a significant advancement over the prior art fixation implants such as wires, screws, expanding nitinol implants and multi-component implants in: (1) the method of operation of the implant and its high strength, (2) the method of insertion of the implant, (3) its compressive and expansion force temperature independence, (4) its efficient implant retention and delivery system, (5) its compatibility with reusable or single use product configuration where all required instruments are sterile packaged with the implant, (6) its efficient and cost effective manufacturing methods, and (7) its minimization of the steps required to place the device. These advantages are important to musculoskeletal surgery as well as industrial applications.

Although the description above contains many specificities, these should not be construed as limiting the scope of the embodiments but as merely providing illustrations of some of the presently preferred embodiments. Thus the scope of the embodiment should be determined by the appended claims and their legal equivalents, rather than by the examples given.

What is claimed is:

1. A fixation device comprising:
   (a) a body that is operable to change shape to expand and shorten the body, wherein
      (i) the body comprises an elastic material;
      (ii) the body has a plurality of prongs on each of a first end and a second end;
      (iii) the body has a shortening section between the prongs on the first end and the second end; and
      (iv) the shortening section is operable to shorten the body by moving from an elongated position to a shortened position; and
   (b) an internal mandrel or an external sleeve, wherein
      (i) the shortening section is held under constraint in the elongated position with the internal mandrel or the external sleeve.

2. The fixation device of claim 1, wherein the body is a tubular shape.

3. The fixation device of claim 1, wherein the shortening section forms an expanded bulge when operated to shorten the body.

4. The fixation device of claim 3, wherein the expanded bulge is oriented with the long axis of the body.

5. The fixation device of claim 1 wherein the fixation devices comprises the internal mandrel, and the shortening section is held in the elongated position with the internal mandrel.

6. The fixation device of claim 5, wherein
   (a) the internal mandrel comprises a cross sectional shape in a first section of the internal mandrel, and
   (b) the first cross sectional shape is different in shape than other sections of the internal mandrel.

7. The fixation device of claim 6, wherein the cross sectional shape is selected from the group consisting of a square shape, a rectangular shape, a hexagonal shape, a triangular shape, and a non-round shape.

8. The fixation device of claim 5 further comprising a lock plate and a lumen, wherein the lock plate is integral to the lumen.

9. The fixation device of claim 8, wherein the lock plate is operable to interact with the internal mandrel so that the lock plate is operable to rotate between a locked position and an unlocked position.

10. The fixation device of claim 1 further comprising a plurality of fenestrations and a lumen, wherein the fenestrations provide openings into the lumen.

11. The fixation device of claim 10, wherein the fenestrations and lumen are positioned to allow bone ingrowth into the body.

12. The fixation device of claim 1, wherein the first end is slotted and the second end is slotted so that each of the first end and the second end is capable of bending to conform to the internal anatomy of bone.

13. The fixation device of claim 1, wherein the prongs in the plurality of prongs extend outward from the body.

14. The fixation device of claim 13, wherein the prongs are twisted in a twist direction.

15. The fixation device of claim 14, wherein the twist direction of the prongs are positioned so that when the body is turned in a first direction the prongs deflect inward.

16. The fixation device of claim 15, wherein the twist direction of the prongs are positioned so that when the body is turned in a second direction the prongs deflect outward.

17. The fixation device of claim 1, wherein the fixation device is operable for use in a medical procedure.

18. The fixation device of claim 1, wherein the elastic material comprises an elastic metal selected from the group consisting of nitinol, stainless steel, titanium, and alloys thereof.

19. The fixation device of claim 1, wherein the elastic material comprises an elastic polymer selected from the group consisting of polyetheretherketone, silicone elastomer, polyethylene, and combinations thereof.

20. A fixation device comprising:
   (a) a body that is operable to change shape to expand and shorten the body, wherein
      (i) the body comprises an elastic material;
      (ii) the body has a plurality of prongs on each of a first end and a second end;

(iii) the body has a shortening section between the prongs on the first end and the second end; and (iv) the shortening section is operable to shorten the body by moving from an elongated position to a shortened position; and (b) an internal mandrel or an external sleeve, wherein (i) the shortening section is held in the elongated position with the internal mandrel or the external sleeve, and (ii) the fixation devices comprises the external sleeve, and the shortening section is held in the elongated position with the external sleeve.

\* \* \* \* \*